United States Patent [19]

Sykes et al.

[11] 4,362,814

[45] Dec. 7, 1982

[54] PROCESS FOR PREPARING 1-CARBA-2-PENEM-3-CARBOXYLIC ACID

[75] Inventors: Richard B. Sykes, Belle Mead; Jerry S. Wells, Ringoes; William L. Parker, Pennington, all of N.J.

[73] Assignee: E. R. Squibb & Sons, Inc., Princeton, N.J.

[21] Appl. No.: 332,056

[22] Filed: Dec. 18, 1981

[51] Int. Cl.$^3$ ............................................. C12P 17/18
[52] U.S. Cl. ..................................... 435/119; 435/880
[58] Field of Search ................................ 435/119, 880

[56] References Cited

U.S. PATENT DOCUMENTS 4,207,395  6/1980  Cassidy et al. ...................... 435/119
4,247,640  1/1981  Kempf et al. ....................... 435/119

OTHER PUBLICATIONS

JACS, 100, 8006 (1978).
J. Antibiotics, 34:1224 (1981).

*Primary Examiner*—Alvin E. Tanenholtz
*Attorney, Agent, or Firm*—Lawrence S. Levinson; Donald J. Barrack

[57] ABSTRACT

Culturing aerobically Serratia sp. SC 11,482 A.T.C.C. No. 39006 in a culture medium containing assimilable carbon and nitrogen sources yields 1-carba-2-penem-3-carboxylic acid.

2 Claims, No Drawings

PROCESS FOR PREPARING 1-CARBA-2-PENEM-3-CARBOXYLIC ACID

BACKGROUND OF THE INVENTION

Th antibiotic 1-carba-2-penem-3-carboxylic acid is reported by Cama and Christensen in *JACS*, 100, 8006 (1978). 1-Carba-2-penem-3-carboxylic acid is prepared chemically, and prior to this invention, has not been found in nature.

1-Carba-2-penem-3-carboxylic acid, p-nitro-benzyl ester can be prepared from the corresponding free acid and can be used to prepare various 2-substituted-1-carba-2-penem-3-carboxylic acids which have antibacterial activity; see Basker, et al., *J. Antibiotics*, 34:1224 (1981).

SUMMARY OF THE INVENTION

The antibiotic 1-carba-2-penem-3-carboxylic acid (systematic name: 7-oxo-1-azabicyclo[3.2.0]hept-2-ene-2-carboxylic acid), i.e.,

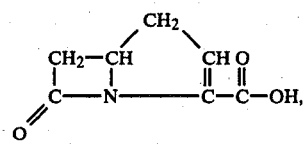

can be produced by culturing aerobically Serratia sp. SC 11,482 in a culture medium containing carbon and nitrogen sources until 1-carba-2-penem-3-carboxylic acid is accumulated and then recovering the antibiotic from the medium.

DETAILED DESCRIPTION OF THE INVENTION

The microorganism used in the present invention is a strain belonging to the genus Serratia that is isolated from plants and salt marsh water. The strain, designated as Serratia sp. SC 11,482, has been deposited as no. 39006 in the permanent collection of the American Type Culture Collection, Rockville, Maryland. A sample of the microorganism can be obtained from that institution. In addition to the specific microorganism described herein, it should be understood that mutants of the microorganism (e.g., mutants produced through the use of x-rays, ultraviolet radiation or nitrogen mustards) can also be cultured to produce 1-carba-2-penem-3-carboxylic acid.

The following is a descrption of Serratia sp. Sc 11,482 A.T.C.C. No. 39006. The procedures for characterization of the organism are those recommended by Grimont, P.A.C. et al., *J. Gen. Microbiol.*, 98:39–66 (1977).

(I) Morphology

The organism is a Gram-negative rod which is motile by peritrichous flagella (Leifson's stain).

On Bennett's agar, colonies initially appear pasty white then developing a pink pigment in the center after about 48 hours. The pigment is produced at 23°–28° C. but is absent when the culture is grown at 37° C. On glycerol-poptone agar the colonies are deeply pigmented from cherry red to reddish purple.

(II) Characterization of the Pigment

The pigment was extracted from cells of Serratia sp. SC 11,482 A.T.C.C. No. 39006 grown on glycerol-peptone agar by the method of Williams, R. P. et al. (1956) *J. Bacteriol.*, 71:115–120. The crude pigment extract along with that obtained from a known strain of *Serratia marcescens* was chromatographed on a silica gel thin layer (Eastman Chromagram) plate. The developing solvent was toluene-ethyl acetate. [1:1]. The pigments of both Serratia sp. SC 11,482 A.T.C.C. No. 39006 and *Serratia marcescens* resolved into two components: the main one appearing as a pinkish red spot with $R_f$ of 0.75; the minor component was pale lavender and remained at the origin. The red pigment fraction from the crude extract was eluted from a silica gel column with the same solvent above, was concentrated in vacuo and dissolved in 2 ml of ethanol acidified with 1N hydrochloric acid (10:1 v/v). The main pigments of Serratia sp. SC 11,482 A.T.C.C. No. 39006 and *Serratia marcescens* both exhibited a sharp spectral peak at 535 nm, which is the characteristic peak of prodigiosin.

(III) Biochemical Characteristics

Serratia sp. SC 11,482 A.T.C.C. No. 39006 is positive for the following biochemical characters: ornithine decarboxylase; acetoin production; lipolysis on Tween 80; Simmon's citrate; aesculin hydrolysis; acid from mannitol, sorbitol, xylose, arabinose, melibiose and sucrose; growth on Difco marine agar and nutrient agar +4% sodium chloride.

Serratia sp. SC 11,482 A.T.C.C. No. 39006 is negative for the following properties: cytochrome oxidase; DN-ase; lysine decarboxylase, arginine decarboxylase (method of Moeller); methyl red; growth on potassium cyanide; production of hydrogen sulfide on triple sugar iron agar and cysteine; gluconate; chitinase; acid from inositol, adonitol, arabitol and α-methyl glucoside.

(IV) Differentiation of Serratia sp. SC 11,482 A.T.C.C. No. 39006 From other Genera The production of prodigiosin in the gramnegative bacteria is limited presently to the genera Alteromonas, Beneckia, Serratia and Vibrio.

Serratia sp. SC 11,482 A.T.C.C. No. 39006 can be differentiated from *Alteromonas rubra* and *Beneckia gazogenes* in that the latter two are obligately halophilic polar flagellates. It differs from *Vibrio psychroerythrus* in that the latter is an obligate halophilic psychrophile (no growth above 20° C.). Serratia sp. SC 11,482, A.T.C.C. No. 39006 is mesophilic growing optimally between 25°–30° C., and while halotolerant (up to 4% sodium chloride), does not require salt for growth. These two properties are also shared by members of the genus Serratia.

Within the genus Serratia three pigmented species are recognized: *Serratia marcescens, Serratia marinorubra* (syn. *rubidaea*) and *Serratia plymuthica* (see Grimont, P.A.D. et al., *J. Gen. Microbiol.*, 98:39–66) (1977). The following table summarizes the key characteristics differentiating Serratia sp. SC 11,482 A.T.C.C. No. 39006 from the other pigmented species in Serratia.

| CHARACTERS | Serratia sp. | Serratia marcescens | Serratia marinorubra A.T.C.C. | Serratia ply muthica A.T.C.C. |
|---|---|---|---|---|
| STRAIN NO. | SC 11,482 | SC 12,360 | 27,614 | 183 |
| DN—ase | − | + | + | + |
| Gelatinase | − | + | + | + |
| Chitinase | − | + | − | + |
| Lysine decarboxylase | − | + | + | − |
| Ornithine | + | + | − | − |

-continued

| CHARACTERS STRAIN NO. | Serratia sp. SC 11,482 | Serratia marcescens SC 12,360 | Serratia marinorubra A.T.C.C. 27,614 | Serratia plymuthica A.T.C.C. 183 |
|---|---|---|---|---|
| decarboxylase | | | | |
| Hydrogen Sulfide | − | + | − | + |
| Gluconate | − | + | + | + |
| Acid from Adonitol | − | − | + | − |
| Arabinose | + | − | + | − |
| Melibiose | + | − | + | + |

Legend
+: positive for character
−: negative for character

(V) Isolation of Microorganism

Serratia sp. SC 11,482 A.T.C.C. No. 39006 were isolated from plant samples containing the bacterium by placing approximately 1 gram of the plant root or stem sample in 100 ml of sterile saline, mixing, and then preparing a series of dilutions in sterile saline. Dilutions were then spread-plated onto the following agar media in order to obtain isolated colonies:

| | | Grams |
|---|---|---|
| (1) | Yeast Extract | 5.0 |
| | Glucose | 10.0 |
| | Crude Agar | 12.5 |
| | Plant Extract | 400 |
| | Distilled Water | 600 |
| (2) | Yeast Extract | 5.0 |
| | Glucose | 10.0 |
| | Agar | 17.5 |
| | Compost Extract | 400 |
| | Tap Water | 600 |
| (3) | Glycerol | 20.0 |
| | Glycine | 2. |
| | NaCl | 1. |
| | K$_2$HPO$_4$ | 1. |
| | FeSO$_4$.7 H$_2$O | 0. |
| | MgSO$_4$.7 H$_2$O | 0. |
| | CaCO$_3$ | 0. |
| | Distilled water to 1 liter | |
| | pH adjusted to 7.0 | |

The media were autoclaved at 121° C. for 30 minutes.

Serratia sp. SC 11,482 A.T.C.C. No. 39006 were isolated from salt marsh water samples containing the bacterium by filtering 50 ml of the sample through a Millipore filter, washing the cells from the filter pad and spread-plating onto a medium containing:

| | Grams |
|---|---|
| L-arginine | 1.0 |
| Glycerol | 12.5 |
| K$_2$HPO$_4$ | 1.0 |
| NaCl | 1.0 |
| MgSO$_4$.7H$_2$O | 0.5 |
| FeSO$_4$.7H$_2$O | 0.01 |
| CuSO$_4$.5H$_2$O | 0.001 |
| ZnSO$_4$.7H$_2$O | 0.001 |
| MnSO$_4$.7H$_2$O | 0.001 |
| Distilled water to 1 liter | |
| pH adjusted to 7.0 | |

The medium was autoclaved at 121° C. for 30 minutes.

After 3 days incubation at room temperature, colonies of Serratia sp. SC 11,482 A.T.C.C. No. 39006 were isolated from the plated samples. The isolated colonies were then grown on a medium containing:

| | Grams |
|---|---|
| Yeast Extract | 1.0 |
| Beef Extract | 1.0 |
| NZ Amine-A | 2.0 |
| Glucose | 10.0 |
| Agar | 15.0 |
| Distilled water to 1 liter | |
| pH adjusted to 7.3 | |

The medium was autoclaved at 121° C. for 30 minutes.

Fermentation of the Microorganism, Isolation of the Antibiotic, and Structure Determination of the Antibiotic The antibiotic 1-carba-2-penem-3-carboxylic acid is produced by cultivating Serratia sp. SC 11,482 A.T.C.C. No. 39006 at, or near, room temperature (about 25° C.) under submerged aerobic conditions in an aqueous nutrient medium containing an assimilable carbohydrate and nitrogen source. The fermentation is carried out for about 18 hours.

The following is a detailed description of the fermentation of Serratia sp. SC 11,482 A.T.C.C. No. 39006 and the isolation of the resulting antibiotic.

(I) Flask Fermentation

Serratia sp. SC 11,482 A.T.C.C. No. 39006 was maintained on the following sterilized medium (A):

| | Grams |
|---|---|
| Yeast Extract | 1 |
| Beef Extract | 1 |
| NZ Amine-A | 2 |
| Glucose | 10 |
| Agar | 15 |
| Distilled H$_2$O to 1 liter | |

Adjust pH to 7.3 before sterilization at 121° C. for 30 minutes.

A loopful of surface growth from an agar slant (Medium A) of Serratia sp. SC 11,482 A.T.C.C. No. 39006 was used to inoculate each of three 500 ml Erlenmeyer flasks each containing 100 ml of Antibiotic Assay Broth (AAB), (Baltimore Biological Laboratory, Cockeysville, Maryland).

After inoculation, the flasks were then incubated at 25° C. on a rotary shaker (300 rpm; 2 inch stroke) for approximately 24 hours. After the appropriate incubation, as described above, 1% (vol/vol) transfers were made from the grown culture flasks to one hundred 500 ml Erlenmeyer flasks each containing 100 ml of sterilized AAB medium, as described above.

After inoculation, the flasks were incubated at 25° C. on a rotary shaker (300 rpm; 2-inch stroke) for approximately 20 hours. At this time the contents of the flasks were pooled and the broth was centrifuged yielding approximately 9.5 liters of supernatant broth.

(II) Tank Fermentation

A loopful of surface growth from agar slant (Medium A) of Serratia sp. SC 11,482 A.T.C.C. No. 39006 was used to inoculate each of five 500 ml Erlenmeyer flasks each containing 100 ml of sterilized AAB medium. The flasks were then incubated at 25° C. on a rotary shaker (300 rpm; 2 inch stroke) for approximately 24 hours. A 1% (vol/vol) transfer of the grown culture broth was made to a FM-75 Fermatron, fermentor (New Brunswick Scientific Co., Edison, New Jersey) containing 50 liters of sterilized AAB medium. After inoculation the fermentation was continued under the following conditions: temperature, 25° C.; pressure, 10 psig; aeration, 1.8 cubic feet/minute; agitation, 200 revolutions/minute. Ucon was added as needed as an antifoam agent. After approximately 20 hours the fermentation was completed. The broth content of the tank was centrifuged yielding approximately 45 liters of supernatant broth.

(III) Isolation of 1-Carba-2-penem-3-Carboxylic Acid from a 10-Liter Fermentation The supernatant broth from the above flask fermentation (9.5 liters, pH 7.13) was stirred at 5° C. with 450 g (wet weight) of Amberlite XAD-2 for 1 hour. The resin was removed by filtration and the filtrate stirred at 5° C. with 180 g (dry weight) of Fisher cocoanut charcoal for 1 hour. The charcoal was separated and washed with cold water, giving 320 g (wet weight) of loaded charcoal. 1-Carba-2-penem-3-carboxylicacid can be stored in this form at $-90°$ C.

A 50 g portion (wet weight) of loaded charcoal was stirred with 250 ml of acetone-water, 7:3, at room temperature for 1 hour, maintaining the pH at 7.7±0.1 by the addition of 1 M NaOH (1.5 ml). The charcoal was removed by filtration and the filtrate concentrated to 22 ml in vacuo at 20° C. The concentrate was applied at 5° C. to a 1.1×6.2−cm column of 200-400 mesh Dowex 1-X8, chloride form, and the colum eluted at 1 ml/minute with a linear gradient prepared from 104 ml of water and 100 ml of 1M NaCL, collecting 2.5 ml fractions. Fractions 20–29 (active against *E. coli* SC 12,155) were combined and applied at 5° C. to a 2.5×23−cm column of 75-150μ CHP20P resin (Mitsubishi Chemical Industries). The column was eluted with water at 1 ml/minute collecting 5 ml fractions. NaCl eluted in fractions 16–24 and 1-carba-2-penem-3-carboxylic acid in fractions 26–35. The active fractions were combined and the resulting solution (47 ml) was passed through a 2 ml column of 100-200 mesh AG MP-1resin, chloride form (Bio-Rad) at 5° C. All activity was retained on the resin. The resin was washed with water and acetonitrile and was dried by passing nitrogen through the bed for 15 minutes giving 0.42 g of dry resin. The loaded resin was stored in this form at $-90°$ C. until needed and then eluted with 0.5 M NaCl (8 ml per gram of loaded resin).

(IV) Isolation of 1-Carba-2-penem-3-carboxylic Acid from a 50-Liter Fermentation Broth supernate from the above 50-liter tank fermentation (45 liters) was stirred with 3 liters of Amberlite XAD-2 resin at 5° C. for 1 hour. The mixture was filtered and the filtrate was stirred with 1.2 kg (dry weight) of Fisher cocoanut charcoal (50-200 mesh) at 5° C. for 1.5 hours. The charcoal was separated, washed with cold water, and then stirred with 8 liters of acetone-water, 7:3, at room temperature for 1 hour, maintaining the pH at 7.7 by the addition of 6N NaOH. The mixture was filtered and the filtrate concentrated in vacuo to 1.5 liters at 20° C. The resulting concentrate was applied at 5° C. to a 2.5×41−cm column of Dowex 1-X8 resin (Cl− form, 200-400 mesh) at 10 ml/min. The column was washed with 50 ml of cold water and then eluted (5° C., 10 ml/min) with a linear gradient prepared from 3740 ml of water and 3600 ml of 1M NaCl, collecting 20 ml fractions. Active fractions (78–98) were combined and shaken with 21 g of Fisher cocoanut charcoal at 5° C. for 1.5 hours, maintaining the pH at 7 by the addition of 1M HCl. The charcoal was separated, washed with cold water and then stirred at 0° C. with 200 ml of acetone-water, 7:3, for 1 hour (pH 7.50). The mixture was filtered and the filtrate concentrated in vacuo at 20° C. to 76 ml. This solution was applied at 5° C. and 2 ml/min to a 1.1×21−cm column of Bio-Rad AG MP-1 resin (Cl− form, 100–200 mesh). The resin was washed with 50 ml of cold water and 100 ml of acetonitrile and was then dried in vacuo (20° C.) giving 5.36 g of loaded resin. The loaded resin was stored at $-90°$ C.

(V) Characterization of 1-Carba-2-penem-3-carboxylic Acid as the p-Nitrobenzyl Ester 1-Carba-2-penem-3-carboxylic acid, sorbed on MP-1 resin, prepared as described in section IV, 5.36 g, was mixed with a solution of 5.4 g of p-nitrobenzylbromide in 10 ml of dry dimethylformamide. The slurry was left at room temperature for 2 hours and then mixed with xylenes (mixture of isomers) and filtered, washing the resin with xylenes. The filtrate was taken to dryness in vacuo (20° C.), removing dimethylformamide azeotropically with xylenes. The residue was dissolved as much as possible (at 20° C.) in 50 ml of toluene, filtered, and the filtrate applied to a 2.5×7−cm column of Mallinckrodt silicic acid (100 mesh) packed in toluene. The column was eluted at 5° C. with 50 ml of toluene followed by 300 ml of toluene-ether, 14:1, collecting 20-ml fractions. Fractions 13–15 contained the ester and were combined and concentrated in vacuo, giving 13.4 mg of crystalline residue. Three recrystallizations from acetone-ether gave 5.7 mg of 1-carba-2-penem-3-carboxylic acid, p-nitrobenzyl ester as a pale yellow solid: melting point 119° to 121° C.; uv max (CH$_3$CN) 270 nm ($\epsilon$ 13,100); $[\alpha]^{22}_{(\lambda)}$ (c 0.3, toluene) +104° (589), 110° (579), 128° (546), 248° (436 nm); ir (CDCl$_3$) 1783, 1729, 1609,1525, 1349, 1319, 1276, 1257, 1209, 1161, 1104, and 1011 cm$^{-1}$; nmr (CDCl$_3$) δ 2.89 (m, 2H), 3.01 (dd, J=3.1, −16.6 Hz, 1H), 3.53 (dd, J=5.4, −16.6 Hz, 1H), 4,32 (m, 1H), 5.23 & 5.50 (ABq, J=−13.7 Hz, 2H) 6.59 (t, J=2.7 Hz), 7.61 & 8.23 ppm (ABq, J=8.8 Hz, 4H).

Analysis.Calc'd for C$_{14}$H$_{12}$N$_2$O$_5$: C, 58.34; H, 4.20; N, 9.72. Found: C, 58.48; H, 4.40; N, 9.50.

Materials Used in Above Embodiments:

Amberlite XAD-2 resin: macroreticular styrene-divinylbenzene copolymer, Rohm and Haas Company CHP20P resin: macroreticular styrene-divinylbenzene copolymer, Mitsubishi Chemical Industries Ltd.

Dowex 1-X8 resin: styrene-divinylbenzene copolymer gel resin with CH$_2$N+(CH$_3$)$_3$ groups attached, Dow Chemical Company.

Bio-Rad AG MP-1 resin: macroreticular styrene-divinylbenzene copolymer with CH$_2$N+(CH$_3$)$_3$ groups attached, Bio Rad Laboratories.

What is claimed is:

1. A process for the preparation of 1-carba-2-penem-3-carboxylic acid which comprises culturing aerobically Serratia sp. SC 11, 482 A.T.C.C. No. 39006 in a culture medium containing assimilable carbon and nitrogen sources until 1-carba-2-penem-3-carboxylic acid is accumulated, and then recovering the 1-carba-2-penem-3-carboxylic acid from the medium.

2. A process in accordance with claim 1 wherein the culturing is carried out at about 25° C.

* * * * *